United States Patent [19]

Bross

[11] Patent Number: 4,705,705

[45] Date of Patent: Nov. 10, 1987

[54] PROCESS FOR THE PRODUCTION OF SLIDES WITH DELIMITED REACTION FIELDS, AND THE SLIDES PRODUCED BY THE PROCESS

[75] Inventor: Klaus Bross, Freiburg, Fed. Rep. of Germany

[73] Assignee: Paul Marienfeld KG, Fed. Rep. of Germany

[21] Appl. No.: 853,408

[22] Filed: Apr. 18, 1986

[30] Foreign Application Priority Data

Apr. 26, 1985 [DE] Fed. Rep. of Germany ....... 3515160

[51] Int. Cl.$^4$ .......................... A47G 1/12; G02B 21/34
[52] U.S. Cl. .......................................... 428/13; 156/57; 350/534; 427/271; 428/210
[58] Field of Search .......................... 156/57; 350/534; 427/271; 428/13, 210

[56] References Cited

U.S. PATENT DOCUMENTS

| | | | |
|---|---|---|---|
| 2,801,568 | 8/1957 | Dakin | 350/534 |
| 3,130,099 | 4/1964 | Homburger | 350/534 X |
| 3,498,860 | 3/1970 | Pickett | 350/534 X |
| 3,737,335 | 6/1973 | Feinberg | 156/57 X |
| 3,891,327 | 6/1975 | Welch | 350/534 X |
| 4,447,140 | 5/1984 | Campbell et al. | 350/534 |
| 4,481,246 | 11/1984 | Melisz et al. | 428/210 |
| 4,545,831 | 10/1985 | Ornstein | 156/57 |

OTHER PUBLICATIONS

*Transplantation*, vol. 25, No. 6 (1978), pp. 331-334.
*Transplantation*, vol. 28, No. 3 (1979), pp. 257-259.

*Primary Examiner*—Robert A. Dawson
*Attorney, Agent, or Firm*—Lowe Price LeBlanc Becker & Shur

[57] ABSTRACT

A process for the production of slides with one or more reaction fields, which are bounded by a hydrophobic surface coating and which, for the fixing of the preparations to be examined, are coated with substances having an affinity therefore is characterized in that
 (a) the regions of at least one surface of the slide which correspond to the reaction fields to be formed are covered with a material which adheres to the surface and which is removable,
 (b) the entire surface of the slide treated in this manner is coated with a hydrophobic material,
 (c) the reaction fields are exposed by removal of the covering material, and
 (d) the exposed reaction fields are coated with the substance having an affinity for the preparations to be examined, and the slides obtained by means of this process.

17 Claims, No Drawings

PROCESS FOR THE PRODUCTION OF SLIDES WITH DELIMITED REACTION FIELDS, AND THE SLIDES PRODUCED BY THE PROCESS

DESCRIPTION

This invention relates to a process for the production of slides with one or more reacton fields which are bounded by a hydrophobic surface coating and which, for the fixation of the preparations to be examined, are coated with substances having an affinity therefor, and to the slides which can be produced thereby.

Numerous methods have been described in the literature for the detection of antigens on cells. Their principle is based on the visualization of the reaction of the antigens with the corresponding antibodies by fluorescence, gold particles or development of dyes by means of enzymes. In this connection, the reaction steps are, as a rule, carried out on suspended cells. Evaluation takes place thereafter by means of transmission measuring devices, or by means of a microscope after transfer of the converted cells to a slide.

A description has also already been provided of fixing the cells employed for these detection methods on the slide surface, for example by producing delimited reaction fields, which are in a position to fix the preparations, such as cells, to be examined. Thereby, it becomes possible to carry out several treatment steps in a simple manner and with the application of differing liquid media, and also to record the resulting preparations in a simple manner.

Thus, it is known to cover the surface of a slide with a plastic film, in which one or more reaction fields have been stamped. The slide surface exposed by these apertures in the plastic film is then coated with a substance which is in a position to fix the preparations to be examined, for example with poly-L-lysine (Transplantation, vol. 25, no. 6 (1978), pages 331 to 334). It is furthermore known to produce slides provided with reaction fields by coating the slide surface in the first instance over the full surface with a water-repellent agent, and then eliminating the latter at the reaction fields and by dropping concentrated sulphuric acid and subsequently one drop of 50% sodium hydroxide solution thereon (Transplantation, vol. 28, no. 3 (1979), pages 257 to 259). In this case also, the exposed glass surface of the reaction fields is coated with poly-L-lysine, in order thereby to permit the fixing of viable cells, for example red blood corpuscles.

These slides permit the anchoring of the cells to be treated, which represents a considerable advance as compared with the previously known methods with suspended cells. In particular, simpler handling is achieved in numerous investigations, so that incubations and washing operations can be undertaken in a simple manner and without centrifuging.

However, the previously known slides with reaction fields are not able to provide complete satisfaction, on the one hand in view of their liquid-repellent action of the regions bounding the reaction fields and on the other hand with regard to the fixing of the preparation, in particular cells, to be examined, on the actual surface of the reaction fields.

The object of the present invention thus consists in providing a process of the initially indicated type, which succeedd in providing in a simple manner slides with reaction fields which show an improvement as compared with the conventional products of this type in their differentiation between the repellent area and the area having an affinity for the biological preparations to be examined.

This object is now achieved by the characterizing features of the process according to the present invention and the particularly preferred embodiments of the subject matter of this invention, as well as by the slides which can be produced with the aid of this process.

The subject of the invention is thus a process for the production of slides with one or more reaction fields, which are bounded by a hydrophobic surface coating and which, for the fixation of the preparations to be examined, are coated with substances having an affinity therefor, which process is characterized in that (a) the regions of at least one surface of the slide which correspond to the reaction fields to be formed are covered with a material which adheres to the surface and which is removable, (b) the entire surface of the slide treated in this manner is coated with a hydrophobic material, (c) the reaction fields are exposed by removal of the covering material, and (d) the exposed reaction fields are coated with the substance having an affinity for the preparations to be examined.

In the process according to the invention, the material used in step (a) for covering the regions corresponding to the reaction fields to be formed is preferably a lacquer, an adhesive foil, a soft stamp of for example rubber or plastic material, and/or one or more macromolecular compounds, these materials being distinguished in that after the subsequent treatment in step (b) they may readily be removed again from the slide surface without residue.

In the process according to the invention, use is made, with advantage, of a macromolecular compound, which is insoluble in organic solvents but which may be applied in aqueous solutions without further ado to the slide and, after evaporation of the solvent or drying, adheres to the slide surface and defines the reaction fields which are finally formed. These reaction fields can vary in number and size and also in position on the slide, as is already usual for conventional slides with standard masks printed thereon.

Following the covering of the regions corresponding to the reaction fields to be formed with the aid of the material which adheres to the surface and which is removable, the entire surface of the slide, including the covered regions, is coated with a hydrophobic material which repels water and aqueous media and thus ensures the required delimitation of the reaction fields relative to one another. By means of the covering of the regions corresponding to the reaction fields by means of the material which adheres to the surface and which is removable, there takes place a screening of the slide surface from the further treatment media, and thus a substantial improvement in the properties of the actual reaction fields, whereby improved fixation of the preparations to be examined at the slide surface in the region of the reaction fields may be achieved.

According to the invention, the macromolecular compound used to cover the regions corresponding to the reaction fields preferably comprises one or more alcohol-insoluble macromolecular compounds, such as for example gum arabic, a dextran, hydroxyethyl cellulose or a polysaccharide of high solubility; it is also possible to use mixtures of these products.

As hydrophobic material with which the entire surface of the slide, including the covered regions corresponding to the reaction fields, is covered, there is used a material, which may be applied in the form of a solution in a solvent, which does not dissolve or attack the covering material. With particular advantage there are used, in combination with the macromolecular compound of the above-described type which is used as covering material and which is soluble in water and which is insoluble in alcohols, hydrophobic compounds which are soluble in alcohol and insoluble in aqueous media, such as for example organosilicon parting compounds, such as silicone oils (Siliclad ® and Repelco ®) or polyorganosiloxanes. A solution of a polyorganosiloxane in a propanol/sulphuric acid mixture is used for this purpose with particular advantage, since an improved bond of the polyorganosiloxane with the slide surface may be achieved by this means, especially when the slide consists of glass.

It should be mentioned at this point that, according to the invention, it is possible without further ado to employ slides of plastic materials, such as polymethylmethacrylate or polycarbonate, although glass slides are particularly preferred. With advantage, operations are carried out with slides having a matt glass border, which provides the possibility of applying lettering. By application of a cover glass and sealing, preservation of the preparations becomes possible.

After the application of the hydrophobic compound in the form of a layer to the entrie slide surface, including the covered regions which correspond to the reaction fields to be formed, which is achieved in that a solution of this hydrophobic compound is applied and then the solvent is evaporated, the reaction fields are exposed by lifting the adhering, removable material. This can be achieved by pulling off the adhesive foil, peeling off the lacquer, lifting the stamps and, in particular with the macromolecular compounds which are preferably employed, by using a solvent which is indeed capable of dissolving the macromolecular compound(s) but does not attack the hydrophobic compound which covers the region around the reaction fields. With advantage, there is employed for this latter case an aqueous basic solvent medium, for which surface-active basic detergents for laboratory equipment are particularly suitable, especially the biologically degradable material Extran ®, which is commercially available. Only the macromolecular compound with the hydrophobic coating present thereon is removed by this treatment, as a result of which the slide surface is exposed in the region of the reaction fields. With particular advantage, according to the invention, the exposed slide surface is treated with an alkaline agent, such as with an alkali metal hydroxide or alkaline earth metal hydroxide, especially sodium hydroxide. This treatment can also take place by gentle rubbing of the slide surface with the basic detergent, which treatment causes the slide surface to be rendered alkaline, which is of advantage especially in the case of the slides made of glass.

Following these treatment measures, the reaction fields which are exposed and which are possibly treated with the alkaline medium are then coated in a manner known per se with one or more substances which have an affinity for the preparations to be examined, i.e. which are capable of fixing the biological preparations, such as cells and the like, which are to be examined, at the slide surface. Substances which have been suitable for this purpose are those which on the one hand adhere to the glass surface and on the other hand can bind cells or proteins, examples of such substances being on the one hand basic substances, such as basic proteins or basic dyes, such as poly-L-lysine, spermidine, poly-arginine, Alcian Blue (Serva SG8), which bind the cells as a result of their negative (acid) charge on the cell surface, whereby all types of cells are encompassed, and on the other hand substances which are capable of reacting with specific molecules of the cell surface, such as for example antibodies, especially those which are specific for specified cell membrane antigens. This last-mentioned method is known in the literature as the panning technique, and serves for the isolation of specific types of cells. In this latter case, the material applied with a basic substance, preferably Alcian Blue, as basic dye which is used in pathology for the staining of acidic substances, to the reaction fields, after which the antibodies concerned are applied to the surface coated in this manner. The still available free valencies of the Alcian Blue are subsequently blocked with inert proteins (albumin, gelatin, etc.), in order to avoid a nonspecific reaction of the cells to be examined. Besides Alcian Blue, it is also possible to use other basic dyes, which on the one hand adhere to the glass surface and on the other hand are able to bind negatively charged cells to themselves and thus to the slide surface.

The substances which are used according to the invention and which have an affinity for the preparations to be examined may without further ado be applied from aqueous media to the slides, in the course of which the applied hydrophobic surface coating prevents these substances having an affinity from also being fixed on the surface regions which do not correspond to the reaction fields.

As a result of the sequence, according to the invention, of the process measures, a particularly strong fixing of these substances having an affinity for the biological preparations to be examined is achieved, which permits a substantial improvement in the analytical methods with the application of these slides, since without interference even more process steps and reaction sequences may be carried out and interfering phenomena may be avoided.

According to the invention, it is furthermore possible to achieve a still further improvement in this advantageous effect, in that the bonding of the substances having an affinity for the preparations to be examined to the slide surface is promoted by chemical bonding and/or in that a thicker coating of these materials is produced by multiple application.

By means of the slides produced according to the invention, a substantially stronger bonding of the biological prepartations to be examined to the slide surface is achieved, and by virtue of the strongly hydrophobic regions which bound the actual reaction fields the various preparations are prevented from running into one another. The subject of the invention thus also includes the slides which can be produced in accordance with the process according to the invention and which can be used for numerous investigations, namely:

(1) For morphological investigations of cells following fixing and staining, in a manner similar to the normal smear techniques and cytocentrifuging.

(2) Incubation of the cells with various antibodies against cell membrane antigens for the identification of specific cell populations, with subsequent visualization of the reaction by means of antibody labelling with enzymes (peroxidase), fluorescent dyes or gold particles.

(3) Detection of intracellular antigens by means of labelled antibodies, following drying and fixing of the cells (antinuclear antibodies).

(4) Detection by reactions of the cells with-
   (a) particles such as bacteria, latex particles, acrylic particles etc.
   (b) substances such as dyes, toxins, lectins etc.

(5) Performance of cytochemical reactions for the detection of cellular enzymes, such as peroxidase, esterase, acidic phosphatase, etc.

(6) Embedding of individual cells for electron microscopy.

(7) Coating and processing of tissue sections for pathological examinations.

(8) Freezing of cells on the slide for subsequent examinations or dispatch.

The following example serves for the further explanation of the invention.

EXAMPLE

A slide having a matt glass border is used, to which slide an aqueous solution of gum arabic is applied in such a manner that twelve round reaction fields having a diameter of approximately 4 mm are formed. The solution is then allowed to dry, after which the entire slide surface, with the exception of the matt border, is coated with a polysiloxane/propanol/sulphuric acid solution. After the drying of this silicone solution, the reaction fields are again exposed with the aid of an alakline, biologically degradable detergent (Extran ®), whereupon the glass surface is rendered alkaline by gentle rubbing with this solution or with a sodium hydroxide solution. After washing with distilled water, the exposed reaction fields are coated with a basic dye (Alcian Blue (Serva SG8)). After a period of action of approximately 5 to 15 minutes or longer, the applied solution is removed with isotonic buffer solution.

The slide is now ready to receive the cell suspension. After application of the cell suspension, the cells are left to settle during a period of time of approximately 15 minutes. As a result of this, the cells are fixed at the surface of the reaction fields; this leads to the surprising effect that the cells are bonded so as to be flat on the slide surface, so that they lie in a depth plane for microscopy. After fixing of the cells, the latter can be subsequently treated in a wide variety of ways.

In order to preserve the final preparation, the latter is then coated with glycerin and sealed with a cover glass. The sides of the cover glass are then sealed in an airtight manner with an adhesive (nail varnish).

I claim:

1. Process for the production of slides with one or more reaction fields, which are bounded by a hydrophobic surface coating and which, for the fixation of the preparations to be examined, are coated with subtances having an affinity therefor, characterized in that
   (a) the regions of at least one surface of the slide which correspond to the reaction fields to be formed are covered with a material which adheres to the surface and which is removable,
   (b) the entire surface of the slide treated in this manner is coated with a hydrophobic material,
   (c) the reaction fields are exposed by removal of the covering material, and
   (d) the exposed reaction fields are coated with the substance having an affinity for the preparations to be examined.

2. Process according to claim 1, characterized in that in order to cover the regions corresponding to the reaction fields a lacquer, an adhesive foil, a soft stamp and/or one or more macromolecular compounds are employed.

3. Process according to claim 2, characterized in that use is made of a macromolecular compound in aqueous solution, such compound being insoluble inorganic solvent, and a hydrophobic material in an organic solvent, such hydrophobic material being insoluble in aqueous media.

4. Process according to claim 2, characterized in that use is made of one or more alcohol-insoluble macromolecular compounds.

5. Process according to claim 4, characterized in that gum arabic, a dextran, hydroxyethyl starch, polysaccharides soluble in aqueous media or mixtures thereof are used as alcohol-insoluble macromolecular compound.

6. Process according to claim 2, characterized in that a hydrophobic material which is soluble in alcohol and insoluble in aqueous media is used.

7. Process according to claim 6, characterized in that a polyorganosiloxane is employed as hydrophobic material soluble in alcohol.

8. Process according to claim 7, characterized in that a solution of a polyorganosiloxane in a propanol/sulphuric acid mixture is employed.

9. Process according to claim 3, characterized in that the reaction fields are exposed with an aqueous solvent medium.

10. Process according to claim 9, characterized in that an aqueous, basic detergent is used as aqueous solvent medium.

11. Process according to claim 1, characterized in that the surface of the exposed reaction fields are treated with an alkaline agent, such as an alkali metal hydroxide and/or an alikaline earth metal hydroxide.

12. Process according to claim 1, characterized in that the reaction fields, which are exposed and possibly treated with an alkaline medium, are coated, in a manner known per se, with one or more substances having an affinity for the preparations to be examined.

13. Process according to claim 12, characterized in that basic proteins and/or basic dyes and/or substances which are known per se and which react with molecules of the cell surface, such as antibodies, are used as substance having an affinity for the preparations to be examined.

14. Process according to claim 13, characterized in that poly-L-lysine, spermidine, polyarginine, Alcian Blue or mixtures of these substances are used as substances having an affinity for the preparations to be examined.

15. Process according to claim 1, characterized in that slides of glass or plastic material are employed.

16. Process according to claim 1, characterized in that the adhesion of the substance having an affinity for the preparations to be examined at the slide surface is promoted by chemical bonding and/or a thicker layer of these substances having an affinity is produced by multiple application.

17. A slide produced according to the process of claim 1 and comprising a hydrophobic surface coating containing exposed reaction field regions coated with a substance having an affinity for the preparations to be examined.

* * * * *